US011400021B2

(12) United States Patent
Aiken et al.

(10) Patent No.: US 11,400,021 B2
(45) Date of Patent: Aug. 2, 2022

(54) SYRINGE ASSEMBLY

(71) Applicant: Plas-Tech Engineering, Inc., Lake Geneva, WI (US)

(72) Inventors: Hannah Aiken, Surrey (GB); Christopher Grimes, Essex (GB); Aaron Hirschmann, Lake Geneva, WI (US); Robert Fesus, Lake Geneva, WI (US)

(73) Assignee: Plas-Tech Engineering, Inc., Lake Geneva, WI (US)

( * ) Notice: Subject to any disclaimer, the term of this patent is extended or adjusted under 35 U.S.C. 154(b) by 24 days.

(21) Appl. No.: 15/516,595

(22) PCT Filed: Oct. 2, 2015

(86) PCT No.: PCT/GB2015/052889
§ 371 (c)(1),
(2) Date: Apr. 3, 2017

(87) PCT Pub. No.: WO2016/051198
PCT Pub. Date: Apr. 7, 2016

(65) Prior Publication Data
US 2018/0263852 A1  Sep. 20, 2018

(30) Foreign Application Priority Data
Oct. 3, 2014  (GB) ..................... 1417548

(51) Int. Cl.
*A61M 5/32* (2006.01)
*A61J 7/00* (2006.01)
(Continued)

(52) U.S. Cl.
CPC ........... *A61J 7/0053* (2013.01); *A61J 1/1418* (2015.05); *A61K 9/006* (2013.01); *A61K 31/485* (2013.01);
(Continued)

(58) Field of Classification Search
CPC .... A61J 1/1418; A61J 7/0053; A61M 5/3134; A61M 5/50; A61M 5/5013; A61M 5/502;
(Continued)

(56) References Cited

U.S. PATENT DOCUMENTS 3,506,008 A  *  4/1970  Huck .................... A61J 7/0053
                                                222/81
5,037,393 A  *  8/1991  Ellgass ............... A61M 5/5013
                                                604/110
(Continued)

FOREIGN PATENT DOCUMENTS

DE   102005028992 A1   1/2007
EP     2 165 729 A1    3/2010
(Continued)

OTHER PUBLICATIONS

Examination Report under Section 18(3) from corresponding International application serial No. GB1417548.3, dated Nov. 20, 2019. 7 pages.
(Continued)

*Primary Examiner* — Rebecca E Eisenberg
(74) *Attorney, Agent, or Firm* — Smith Keane LLP

(57) ABSTRACT

An oral dosing syringe assembly comprises a syringe barrel comprising an inner chamber filled or adapted to be filled with medicament, and a channel in fluid communication with the chamber and through which medicament is dispensed. The assembly further comprises an end cap configured to be removably attached to the syringe barrel, characterised in that the barrel comprises an internal threaded section which mutually engages with a threaded section or the end cap to thereby create a seal, which prevents the flow of medicament therethrough.

11 Claims, 8 Drawing Sheets

(51) Int. Cl.
*A61J 1/14* (2006.01)
*A61M 5/31* (2006.01)
*A61K 9/00* (2006.01)
*A61K 31/485* (2006.01)
*A61K 31/5517* (2006.01)

(52) U.S. Cl.
CPC ....... *A61K 31/5517* (2013.01); *A61M 5/3134* (2013.01)

(58) Field of Classification Search
CPC .......... A61M 5/31591; A61M 5/31536; A61M 5/31501; A61M 5/3157
See application file for complete search history.

(56) References Cited

U.S. PATENT DOCUMENTS

| | | | |
|---|---|---|---|
| 5,891,165 A | | 4/1999 | Buckner |
| 5,941,404 A | | 8/1999 | Charrette |
| 2006/0184136 A1 | * | 8/2006 | Kleyman .......... A61M 5/31595 604/210 |
| 2007/0016146 A1 | * | 1/2007 | Yang ................. A61M 25/0631 604/263 |
| 2013/0296779 A1 | * | 11/2013 | Kuehne ............... A61M 5/3134 604/93.01 |
| 2014/0263317 A1 | | 9/2014 | Linder |

FOREIGN PATENT DOCUMENTS

| | | |
|---|---|---|
| GB | 1248636 | 10/1971 |
| GB | 1248636 A | 10/1971 |
| WO | 2005/035045 A1 | 4/2005 |
| WO | 2008/151148 A1 | 12/2008 |
| WO | 2012/129248 | 9/2012 |

OTHER PUBLICATIONS

Examination Report under Section 18(3) from corresponding International application Serial No. 15782024.2, dated Sep. 26, 2018, 3 pages.
Written Opinion of the International Searching Authority corresponding International application serial No. PCT/GB2015/052889, dated Jan. 22, 2016, 3 pages.
UK Intellectual Property Office, Examination Report for Application No. GB1417548.3, dated Feb. 28, 2020, 2 pages.
UK Intellectual Property Office, Examination Report for Application No. GB1417548.3, dated Jun. 29, 2020 3 pages.
UK Intellectual Property Office, Examination Report for Application No. GB1417548.3, dated Sep. 16, 2020, 3 pages.
Nov. 17, 2020 Examination Report regarding related Great Britain patent application No. GB1417548.3, 3 pages.
Dec. 29, 2020 Response to Nov. 17, 2020 Examination Report regarding related Great Britain patent application No. GB1417548. 3, 17 pages.
Mar. 31, 2021 Certificate of Grant regarding related Great Britain patent application No. GB1417548.3, 4 pages.

* cited by examiner

SYRINGE ASSEMBLY

The present invention relates to syringe assemblies, and particularly, although not exclusively, to syringe assemblies for storing and dispensing a medicament. In particular, the syringe assemblies are configured to administer liquid medicament orally, for example either sublingually or buccally. The invention extends to methods of using syringe assemblies for oral (i.e. either buccal or sublingual) delivery of medicament.

Pharmaceutical compositions may be administered to patients via a range of routes including orally, buccally, sublingually, rectally, vaginally, topically and/or transdermally. These routes of administration are advantageous as drugs administered in this way may be absorbed through the mucous membranes, or Stratum corneum and skin layers associated with the sites of delivery. Buccal and sublingual delivery is further advantageous over orally administered medicament as this avoids hepatic first pass metabolism and drugs are not exposed to acidic degradation in the stomach or to enzymatic degradation within the gastrointestinal (GI) tract.

As a result of the benefits provided by administration via the buccal and sublingual route, there has been considerable interest in reformulating drugs which have conventionally been administered by other routes. Additionally, a number of drugs formulated for administration by other routes, such as injectable solutions, have been used to treat patients buccally, for example morphine, midazolam and diamorphine. An example of such a product is Epistatus, which is a composition comprising midazolam (Special Products Limited, UK).

Traditionally, liquid medicaments administered orally, buccally and sublingually may be administered using a syringe or cup being dispensed from a bottle, ointment or an oral spray. However, a medicament may only be administered orally if the patient is cooperative, and this may not always be possible. For example, buccal midazolam is used to treat epileptic patients who are suffering from seizures, and especially prolonged acute convulsive seizures. Accordingly, a patient suffering from a seizure would not be able to cooperate. When a patient is suffering from a seizure, they may bite down, which would make it even harder to administer an oral medicament. Finally, an oral spray will also have draw backs associated with it, as it will be difficult to administer to an uncooperative patient and the patient could inadvertently inhale the spray.

Previously, syringes have been used to administer medicaments buccally, sublingually and orally. In this case, the medicament would generally be provided as a bulk liquid, and a dose of the liquid would be drawn into the syringe and administered to the patient. However, preparing doses in this way can result in an incorrect dose being erroneously drawn from the bulk liquid. Additionally, a number of drugs which are administered buccally are controlled substances. As a requirement of legislation in most countries, access to bulk supplies of such drugs is carefully managed. If a patient is in urgent need of the drug, locating and accessing the bulk supply of the drug will add to the time required to calculate, obtain, prepare and administer the dose.

A further drawback is that once a syringe has been filled and is being taken to the patient, a relatively low amount of pressure on the plunger end of the syringe will result in inadvertent discharge of the medicament. Additionally, most syringes are configured to allow connection to a needle or drip. In particular this generally means that syringes are provided with a screw thread or projection adjacent to the tip which can be connected to a transfer means such as a needle or a drip. When used to administer medicament buccally, this screw thread or projection could cause damage the mucous membrane in a patient's cheek.

Finally, a dose of a medicament intended for buccal administration would often be harmful if it were injected intramuscularly or intravenously. The use of a syringe to deliver the medicament could lead to confusion on the part of the administrator resulting in them administering the medicament via the incorrect route. In a worst case scenario this can result in the death of the patient.

The present invention arises from the inventor's work in trying to overcome the problems associated with oral (especially buccal) administration in the prior art.

In accordance with a first aspect of the invention, there is provided an oral dosing syringe assembly comprising:
  a syringe barrel comprising an inner chamber filled or adapted to be filled with medicament, and a channel in fluid communication with the chamber and through which medicament is dispensed; and
  an end cap configured to be removably attached to the syringe barrel,
characterised in that the barrel comprises an internal threaded section which mutually engages with a threaded section on the end cap to thereby create a seal, which prevents the flow of medicament therethrough.

Advantageously, the positioning of the internal screw threaded section on the barrel (rather than being external and therefore exposed) ensures that the inside of a patient's mouth is not damaged as the medicament is administered. Also, the syringe assembly allows a medicament for oral administration to be stored safely therein (i.e. pre-filled), without the risk of the medicament leaking or the solvent (e.g. ethanol) evaporating due to the threaded end cap (or tip cap). Additionally, the medicament can be administered quickly to the patient without the user needing to pause to measure a dose.

Preferably, the syringe barrel does not comprise attachment means for connection to a medicament transfer means. An attachment means may comprise anything which is configured to allow a medicament transfer means to be attached thereto, thereby enabling the flow of medicament from the chamber and into the transfer means. An attachment means may include a projection and/or screw thread disposed at least adjacent to the end of the syringe barrel from which medicament is dispensed, and configured to be attached to a transfer means. Preferably, therefore, the syringe barrel is incompatible with a Luer lock, or a Luer slip, and the like. For example, a medicament transfer means may include anything that is configured to be attached to the syringe barrel for the transfer of the medicament from the barrel to a patient, such as a needle or a drip.

Preferably, the syringe barrel does not comprise an external screw thread at least adjacent or towards the end of the barrel from which medicament is dispensed, i.e. on the delivery tip. Accordingly, the syringe assembly cannot cause any damage to the buccal cavity of a patient.

Advantageously, this safety mechanism ensures that it is not possible to use the syringe of the invention to administer the medicament intravenously or intramuscularly, which could otherwise cause harm to a patient and might even result in their death.

Thus, in one preferred embodiment, the syringe assembly of the invention is a buccal syringe assembly for administering medicament to a patient's buccal cavity.

In another preferred embodiment, the syringe assembly is a sublingual syringe assembly for administering medicament to a patient sublingually.

Preferably, the syringe assembly comprises a flat tip oral dosing syringe.

Preferably, the internal threaded section of the barrel is surrounded by a wall such that the threaded section is not exposed. Preferably, the outside of the wall is smooth, and is an extension of the outer wall of the barrel. It will therefore be appreciated that the internal threaded section is disposed on the inside of the wall, and that the threaded section extends from the end of the barrel from which medicament is dispensed towards the channel, which leads to the chamber. Preferably, the internal threaded section extends along the longitudinal axis of the barrel.

Preferably, the end cap comprises a body with one or more projection, which extends transversely away therefrom, and which is configured to facilitate removal of the cap from the barrel. Preferably, the body of the end cap comprises at least two mutually opposing projections. The inventors have designed several different embodiments of the end cap, as shown in FIGS. 7-9. As can be seen, the size (and therefore surface area) of the projections increases from FIGS. 7 to 9.

Preferably, the body of the end cap comprises an external threaded section which screws into the internal threaded section of the barrel. Preferably, the body comprises a central bung on which the threaded section is disposed. Accordingly, in use, the cap is screwed onto the end of the barrel by means of the mutual engagement of the internal and external threaded sections. Preferably, a distal portion of the body is configured to create a tight seal in the channel, thereby preventing leakage or unintentional discharge of medicament when the cap is secured on to the barrel.

Preferably, the barrel comprises a transparent or translucent material. The barrel may comprise any polymer that may be injection moulded, such as polypropylene, low density polyethylene (LDPE), high density polyethylene (HDPE), polycarbonate, thermoplastic elastomers, cyclic olefin polymer, cyclic olefin copolymer and blended materials thereof.

The cap may be manufactured by injection moulding plastics such as polypropylene, LDPE, HDPE, polycarbonate, thermoplastic elastomers, cyclic olefin polymer, cyclic olefin copolymer and blended materials thereof.

In one embodiment, the syringe assembly is a single unit dose syringe assembly pre-filled with medicament. Preferably, the medicament is selected from a group of medicaments consisting of: analgesics, anti-convulsants, antidepressants, vasodilators, steroids, opiate antagonists, anaesthetics, antiadrenergic compounds, antiallergic drugs, anti-anginals, anti-asthmatics, antibacterials, anti-coagulants, anti-cholinergics, antiemetics, antiepileptics, antihistaminics, antiinfectives, antiinflammatories, antimigraine drugs, bronchodilators, cardiac depressants, thrombolitics, beta blockers, opioids, sedatives, benzodiazepines and stimulants.

More preferably, the medicament is selected from a group consisting of: midazolam, lorazepam, diazepam, paraldehyde, pentobarbital, morphine, carbamazepine, ethosuximide, clorazepate, clonazepam, felbamate, forphenytoin, gabapentin, lacosamide, lamotrigine, levetiracetam, oxarbacepine, phenobarbital, phenytoin, pregabalin, primidone, tiagabine, topiramate, zonisamide, clobazam, vigabatrin, fentanyl, oxycodone, diamorphine, alprazolam, clonazepam, vasopressin, levetiracetam, and NSAIDs, or a salt thereof.

Most preferably, the syringe assembly is a unit dose syringe assembly pre-filled with midazolam or a salt thereof, such as midazolam maleate.

Preferably, the syringe assembly comprises a plunger configured to slide in the chamber. The plunger can be manufactured by injection moulding plastics. The plunger may suitably be moulded from polypropylene, LDPE, HDPE, polycarbonate, thermoplastic elastomers, cyclic olefin polymer, cyclic olefin copolymer and blended materials thereof.

Preferably, the plunger comprises a rod having first and second ends, wherein the first end is inserted into the chamber, and the second end comprises a thumb tab, and the barrel comprises a finger tab, which is configured to be engaged with the finger of one hand while also engaging the thumb tab with the thumb of the same hand. Hence, preferably the syringe is configured such that when the end cap is detached from the barrel, a user may apply pressure to the finger and thumb tabs, which causes the plunger rod to slide within the chamber and causing the medicament to be dispensed through the channel.

Preferably, the pre-loaded single unit dose syringe assembly is configured to dispense substantially all of the medicament in a single delivery. Preferably, the syringe assembly comprises a transversely extending projection disposed on the side of the plunger rod, and an indentation disposed along the inside of the chamber, or vice versa, wherein alignment of the projection and indentation correlates with a defined volume of medicament and thereby a dosage. Hence, the plunger rod is maintained at the fill volume when not stored. The advantage of the stop therefore helps to ensure that an accurate dosage of medicament is inserted into the chamber during loading. It also stops the plunger rod from being withdrawn from the barrel.

Accordingly, in a preferred embodiment the syringe assembly may be configured to deliver the required different single doses. For example, the plunger can be arranged to deliver 0.25 ml, 0.5 ml, 0.75 ml or 1 ml of medicament.

Hence, in some embodiments the chamber is preferably adapted to hold about 0.1-25 ml of medicament, or more preferably about 0.1-25 ml or about 0.1-10 ml, or about 0.1-5 ml, or about 0.1-2 ml, or about 0.1-1 ml of medicament.

In a second aspect, there is provided the syringe assembly of the first aspect, for use in therapy.

In a third aspect, there is provided the syringe assembly of the first aspect, for use in treating, preventing or ameliorating a seizure.

In accordance with a fourth aspect, there is provided midazolam or a salt thereof, for use in treating a seizure, wherein the midazolam is for buccal administration using the syringe assembly according to the first aspect.

The seizure may be a prolonged acute convulsive seizure, which could result in status epilepticus.

In accordance with a fifth aspect, there is provided morphine, for use in treating pain, wherein the morphine is for oral, preferably buccal, administration using the syringe assembly according to the first aspect.

In accordance with a sixth aspect, there is provided a method of administering a medicament to a patient in need of treatment using a syringe assembly according to the first aspect, the method comprising removing the cap from the barrel; and dispensing medicament from the chamber, to thereby administer the medicament to the patient.

Preferably, the syringe assembly of the first aspect of the invention is used to administer the medicament orally, buccally, sublingually, rectally, vaginally, topically or transdermally. However, buccal administration is preferred.

Hence, according to a seventh aspect, there is provided a method of administering a medicament to a patient in need of treatment using a syringe assembly according to the first aspect, the method comprising: removing the cap from the barrel; inserting an end of the barrel into the mouth of a patient in need of treatment; and applying pressure to the plunger, thereby causing medicament contained in a chamber to be dispensed.

The end of the barrel may be inserted into the patient's buccal cavity or under the patient's tongue.

All features described herein (including any accompanying claims, abstract and drawings), and/or all of the steps of any method or process so disclosed, may be combined with any of the above aspects in any combination, except combinations where at least some of such features and/or steps are mutually exclusive.

For better understanding of the invention, and to show how embodiments of the same may be carried into effect, reference will now be made, by way of example, to the accompanying Figures, in which:

FIG. 1 shows a cross-sectional side view of an embodiment of a syringe assembly according to the invention. The syringe is a flat tip oral dosing syringe and has a slidable plunger disposed in a barrel. They syringe is shown with its threading cap attached thereto;

EXAMPLE

The inventors have designed a novel syringe assembly 2, which Is shown in the Figures. The illustrated assembly 2 includes a flat tip oral dosing syringe, as it is primarily used for the oral delivery (i.e. either sublingual or buccal) of medicament to a patient. The medicament can for example be Epistatus, which is a composition comprising midazolam maleate (Special Products Limited, UK).

Figure 1:
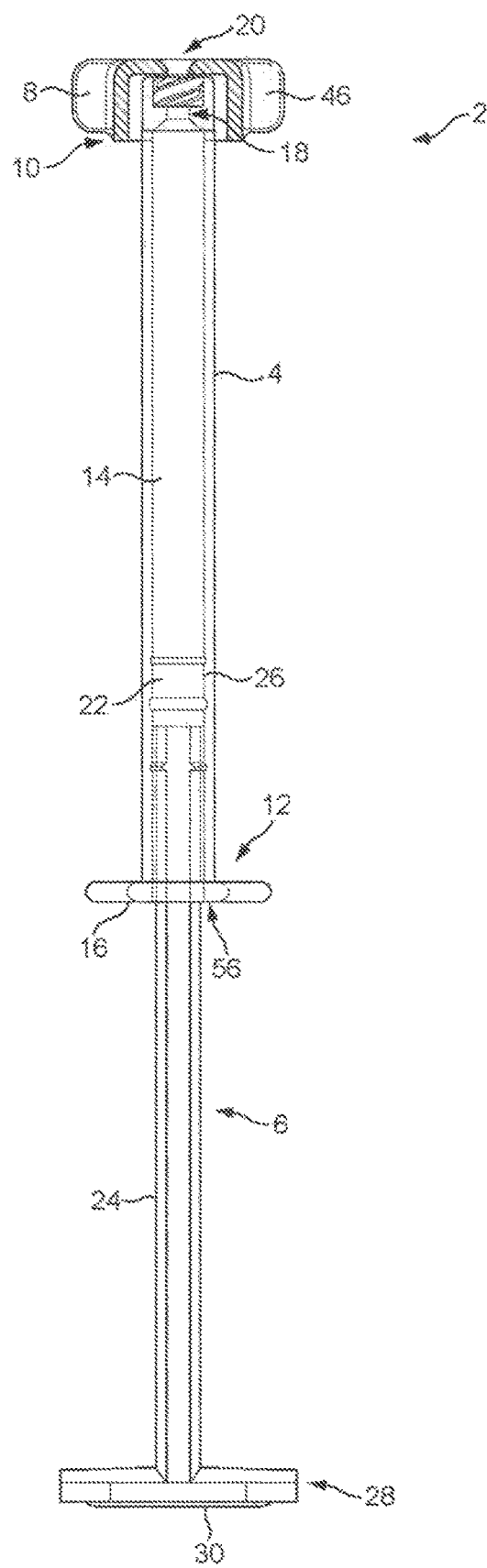

Referring first to FIG. 1, the syringe assembly 2 generally consists of a main barrel 4 into winch a plunger 6 is inserted, and a threading cap 8 which is screwed onto a dispensing end 10 of the barrel 4 when the syringe assembly 2 is not in use. The threading cap 8 is removed from the barrel 4 prior to administration of the medicament to the patient. The dispensing end 10 of the barrel 4 is flat, as is the opposing second end 12, and is therefore known as a flat tip oral dosing syringe. An inner chamber 14 extends through the core of the barrel 4 between the first and second ends 10, 12. The inner chamber 14 is sized so as to hold a desired volume of medicament, for example about 0.1-10 ml medicament.

An outer finger tab 16 is disposed around the circumference of the second end 12 of the barrel 4, and provides a surface against which a user's fingers can apply pressure. In use, once the cap 8 has been removed from the barrel 4, medicament (such as midazolam maleate) stored in the chamber 14 is dispensed through an elongate channel 18 which extends between the chamber 14 and the first end 10 of the barrel 4 and out of tip 20, which is shown most clearly in FIG. 4.

The barrel 4 is made of a transparent or translucent material allowing the patient to see the medicament which is to be dispensed from the chamber 14. The barrel 4 can be manufactured by injection moulding plastics, for example polypropylene, LDPE, HDPE, polycarbonate, thermoplastic elastomers, cyclic olefin polymer, cyclic olefin copolymer and blended materials thereof.

Referring to FIG. 1, the plunger 6 comprises an elongate rod 24 having a first end 26 fitted with a rubber stop 22, which is inserted into the chamber 14 in the barrel 4, and a second opposing end 28 on which is disposed a thumb tab 30 which is sized so as to be operable by a user's thumb. In use, a user depresses the rod 24 to slide along the chamber 14 by exerting pressure on the finger tab 16 with the fingers of one hand. Simultaneously, pressure is applied on the thumb tab 30 with the thumb of the same hand, thereby urging the thumb tab 30 to move towards the finger tab 16 and causing the rod 24 to slide within the chamber 14. An internal rubber seal 56 is disposed at the end of the chamber 14 by the finger tab 16, which provides a good seal with the rod 24 as it slides along the chamber 24. This prevents leakage of medicament.

Figure 2:
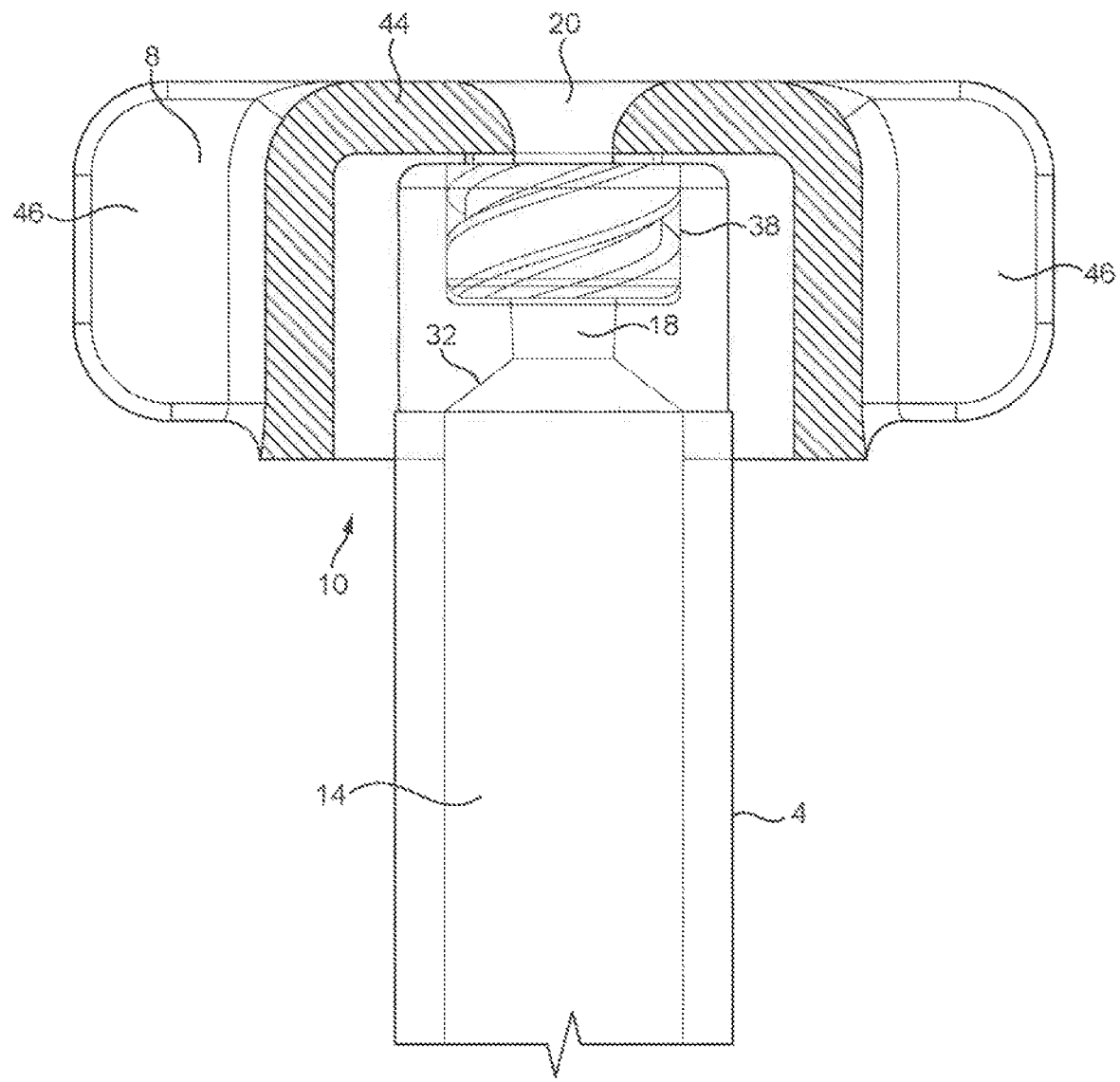
FIG. 2 shows an enlarged cross-sectional side view of the dispensing end of the barrel and threading cap shown in FIG. 1.

In one embodiment, the rod 24 slides within the chamber 14 until the first end 18 of the rod 24 reaches an end stop 32 of chamber 14, as shown in FIG. 2. The rubber stop 22 on the end of the rod 24 ensures that medicament is expelled from the chamber 14 through channel 18 and out of tip 20. This embodiment is known as a single-dose syringe. It should be appreciated that the design of the tip 20 of the syringe 2 is incompatible with a Luer lock or Luer slip and/or a needle, and thereby removes any risk of the syringe assembly 2 being used to administer the medicament intravenously or via a drip, which could harm the patient.

Figure 5:
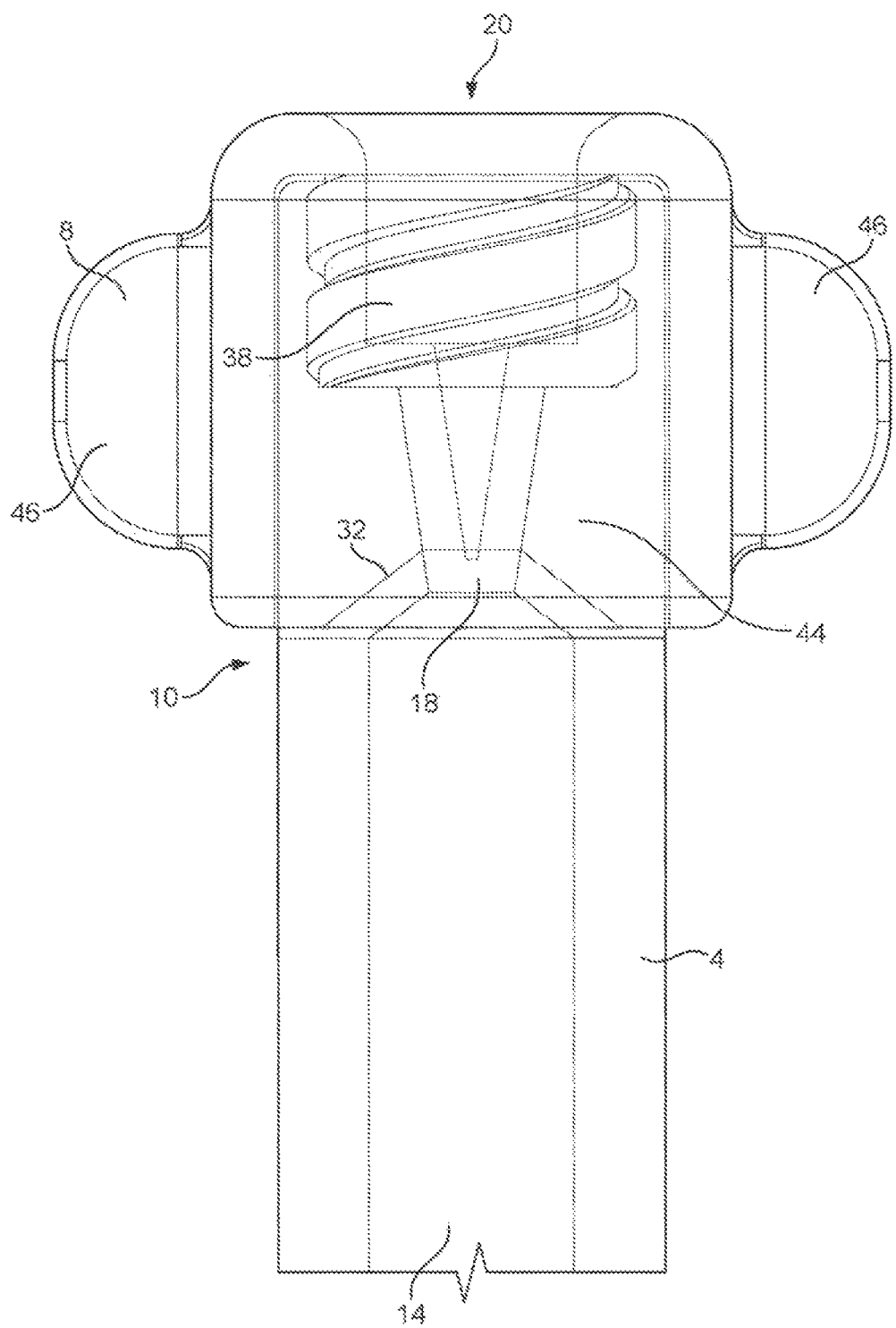
FIG. 5 shows an enlarged cross-sectional side view of the dispensing end of the barrel showing the internal threads and with the cap fitted, illustrating an increased depth in the threaded section.
Figure 6:
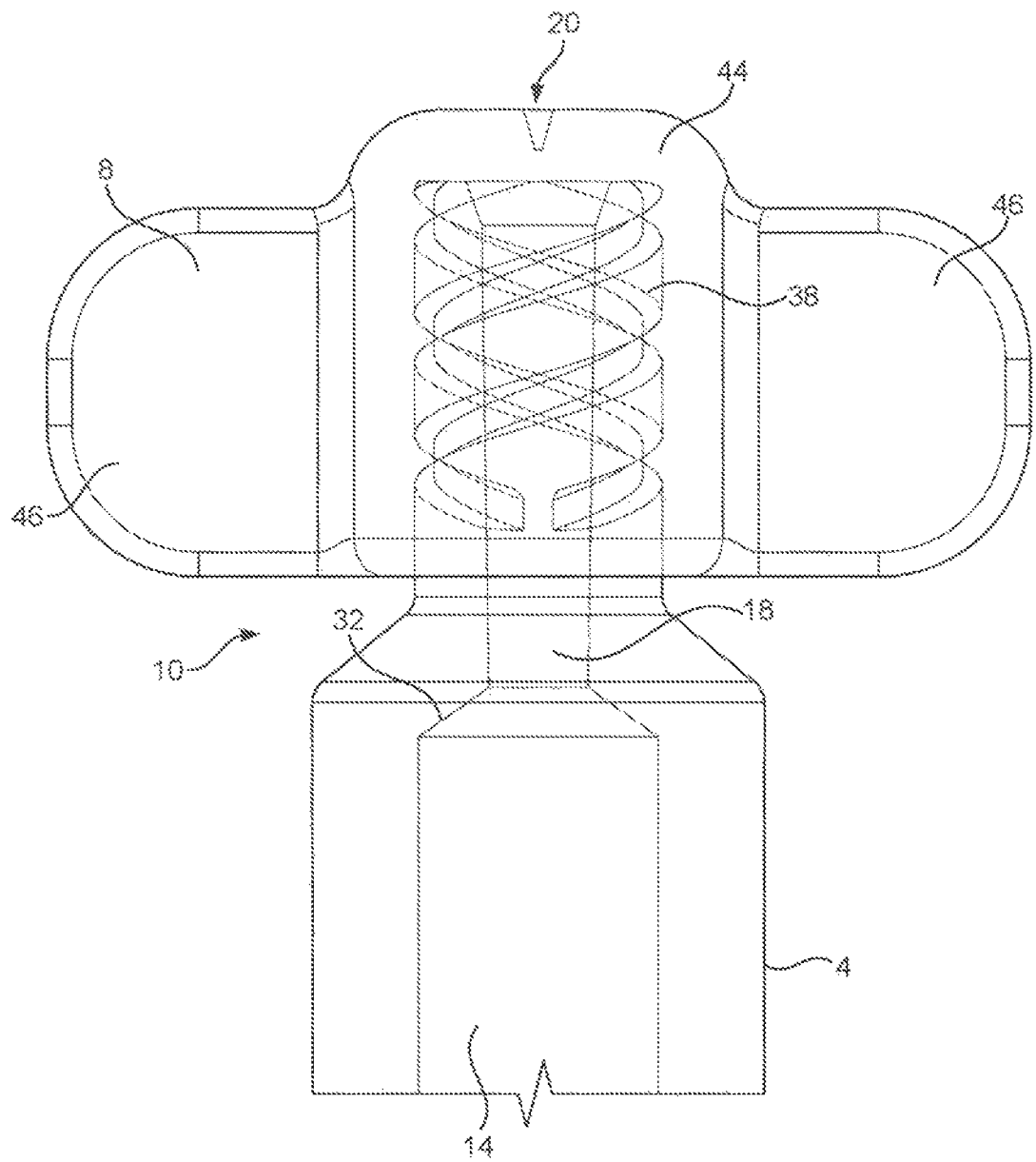
FIG. 6 shows an enlarged cross-sectional side view of the dispensing end of the barrel showing the internal threads and with the cap fitted, illustrating an increased depth in the threaded section and with larger wings on the cap.
Figure 10:
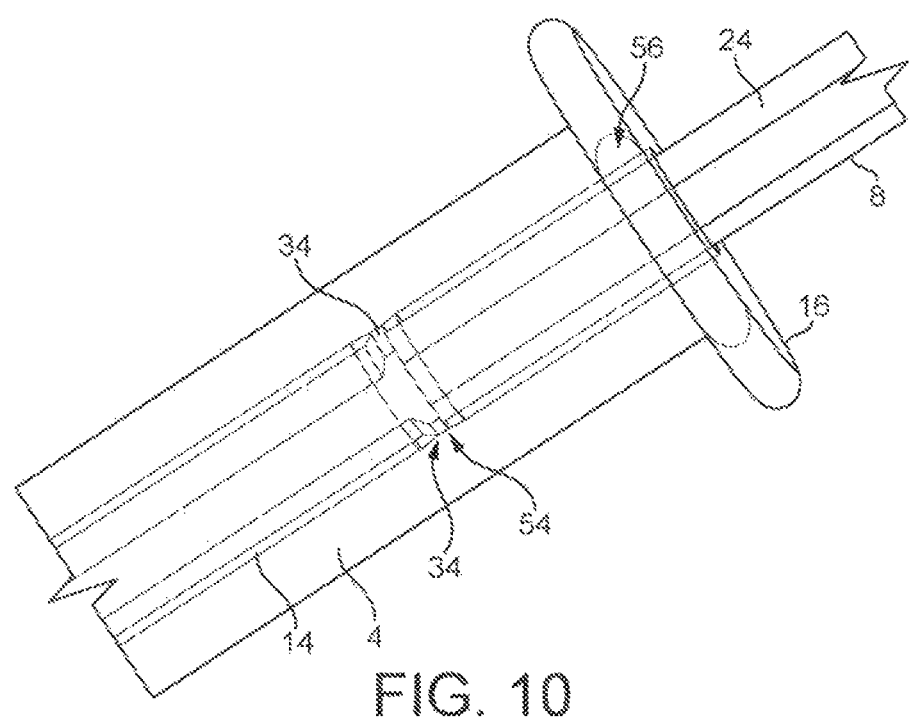
FIG. 10 shows an enlarged cross-sectional side view of the end of a syringe into which the plunger is inserted.

In another embodiment, shown in FIG. 10, a transversely extending projection or stop 34 is disposed on the side of the rod 24, and an indentation 54 is disposed along the inside of the chamber 14, as shown in FIG. 5. The stop 34 and indentation 54 help during loading of the assembly 2 with medicament. Alignment of the stop 34 and indentation 54 correlates with a defined volume of medicament and thereby a dosage. Hence, the plunger rod 24 is maintained at the correct fill volume when not stored. The advantage of the stop therefore helps to ensure that an accurate dosage of medicament is inserted into the chamber 14 during loading. It also stops the plunger rod 24 from being withdrawn from the barrel 4.

For example, the plunger 24 can be arranged to deliver 0.25 ml, 0.5 ml, 0.75 ml or 1 ml medicament. The plunger 8 may be made by injection moulding plastics, for example polypropylene, LDPE, HDPE, polycarbonate, thermoplastic elastomers, cyclic olefin polymer, cyclic olefin copolymer and blended materials thereof.

The syringe 2 can be provided pre-filled with medicament, which can be any medicament suitable for oral, sublingual or buccal administration, such as a composition comprising midazolam maleate (e.g. for treating a seizure). A problem inherent with currently available syringes that are designed to be used for oral administration of a drug is that they have an external threaded section at their dispensing end, which is required to attach the syringe to a Luer lock, or Luer slip, a needle, or a drip etc. As such, problems often occur when using such syringes during buccal or sublingual delivery because lesions are often caused inside the patient's mouth, e.g. on the cheek or under the tongue, during administration of the drug. The syringe assembly 2 illustrated in the Figures overcomes these problems, as described below.

Figure 4:
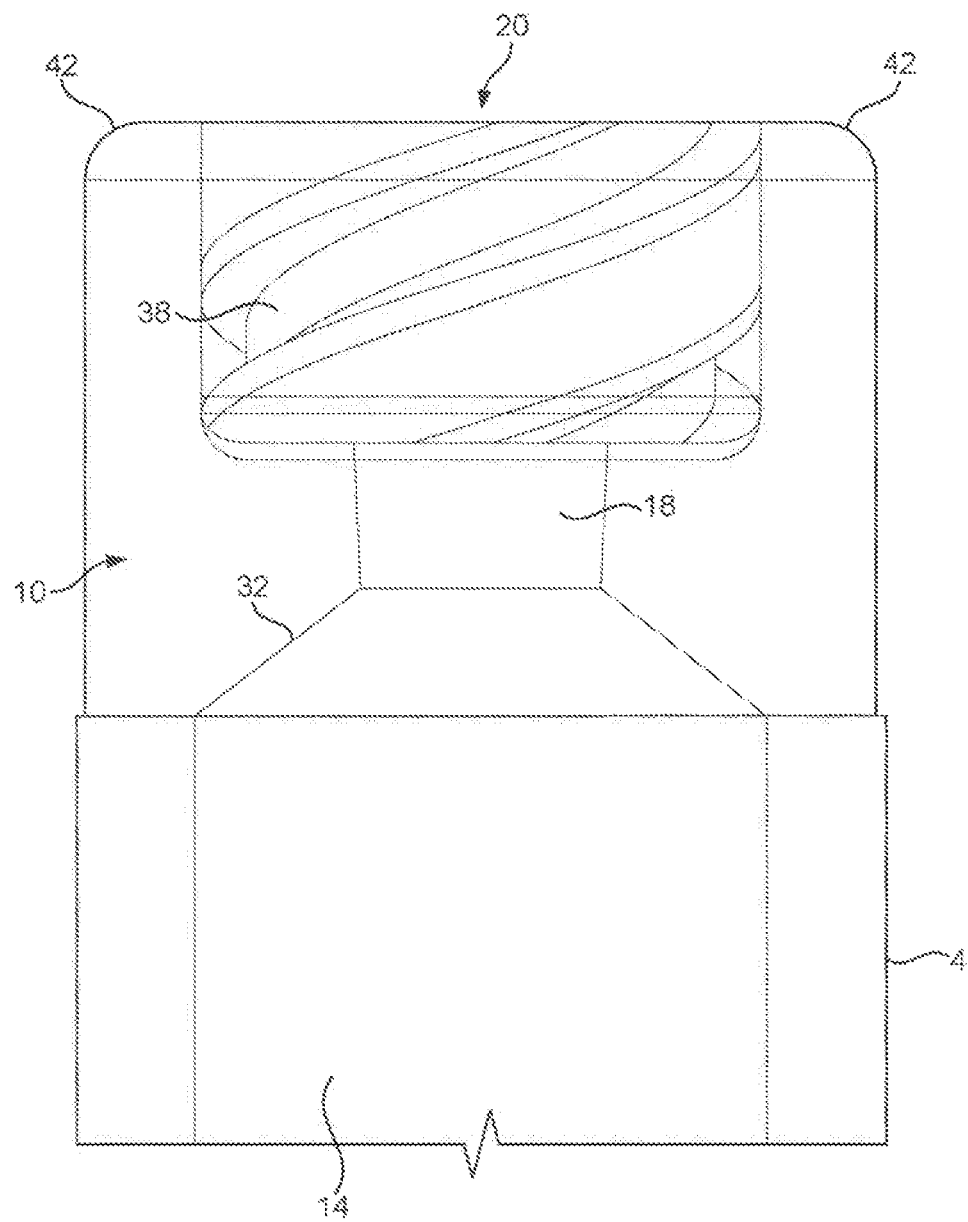
FIG. 4 shows an enlarged cross-sectional side view of the dispensing end of the barrel showing the internal threads without the cap attached.

As can be seen most clearly in FIG. 4, which shows the dispensing end 10 of the barrel 4 without the cap 8 attached, there is provided an internally threaded section 38 surrounded by a wall 42. The threaded section 38 extends along the longitudinal axis of the barrel 4. The outside of the wall 42 is smooth, and is effectively an extension of the outer wall of the barrel 4, whereas the inside of the wall 42 bares the internal screw thread 38, which extends from the tip 20 towards channel 18, which leads to the chamber 14. As can be seen in FIGS. 4 and 5, the length of the channel 18 can vary, as can the length of the internal threaded section 38.

Figure 3:
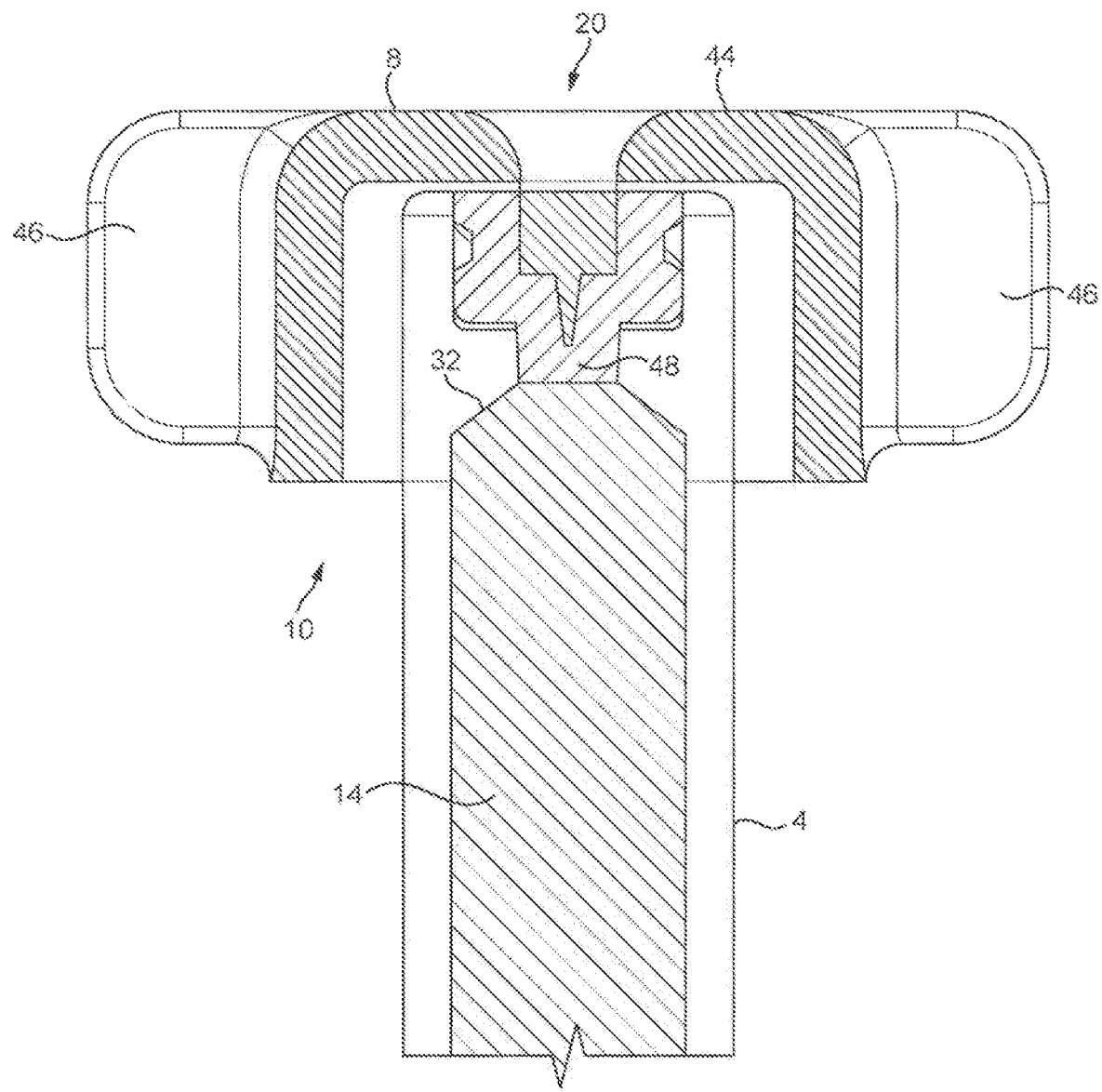
FIG. 3 shows another enlarged side view of the dispending end of the barrel and the threading cap shown in FIG. 1.

Referring now to FIG. 3, there is shown a simplified cross-sectional view of the cap 8, which has a body 44 and two wings 46, which extended transversely away therefrom. Extending from the centre of the body, there is disposed a head section 48 which bears an external thread 40, which screws into the correspondingly threaded section 38 in the dispensing end 10 of the barrel 4. Accordingly, the cap 8 is screwed onto the end 10 of the barrel by means of the mutual engagement of the internal and external thread sections 38, 40. When screwed on to the barrel 4, the distal part of the head section 48 of the cap 8 creates a tight seal in the channel 18, thereby preventing leakage or unintentional discharge of medicament while the cap 6 is secured on to the barrel 4.

Prior to administration of the medicament to a patient, the user first unscrews the cap 8, and then inserts the dispensing end of the barrel 4 into the patient's mouth, for example sublingually or buccally. Due to the internal and therefore unexposed positioning of the threaded section 38, it cannot come into contact with the mucous membrane in the mouth of a patient during drug administration, and so will not cause lesions thereto during use.

Figure 7:
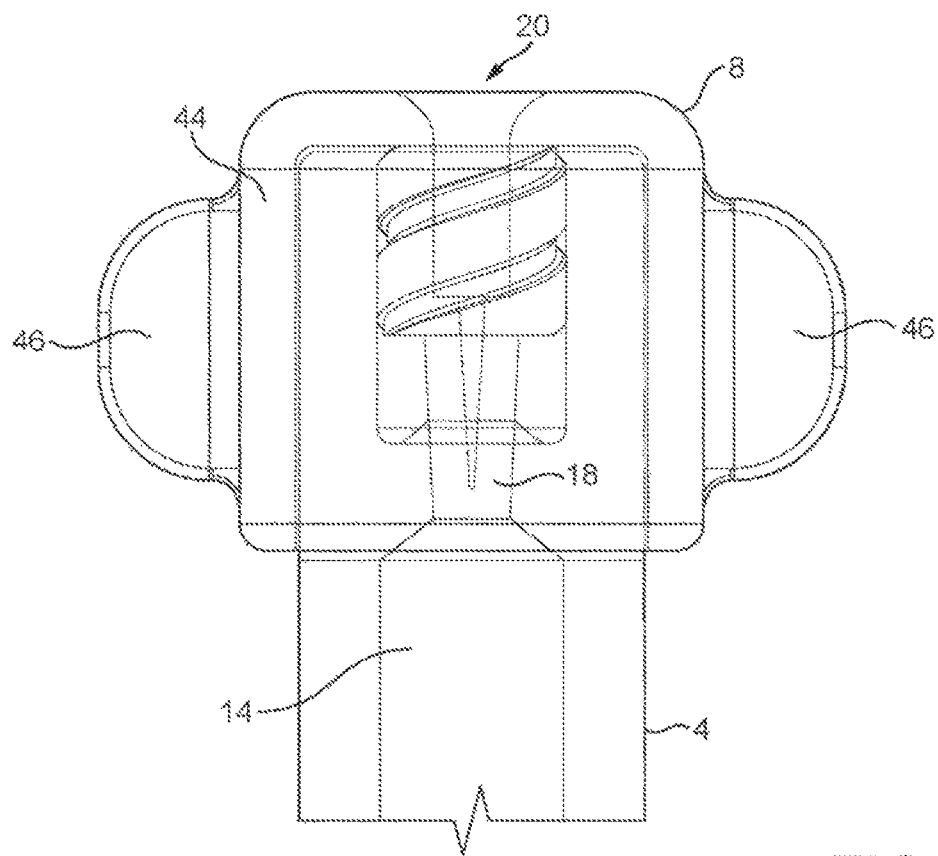
FIGS. 7-9 show an enlarged cross-sectional side view of the dispensing end of the barrel showing the internal threads, and with the cap fitted illustrating increasing wing sizes.
Figure 8:
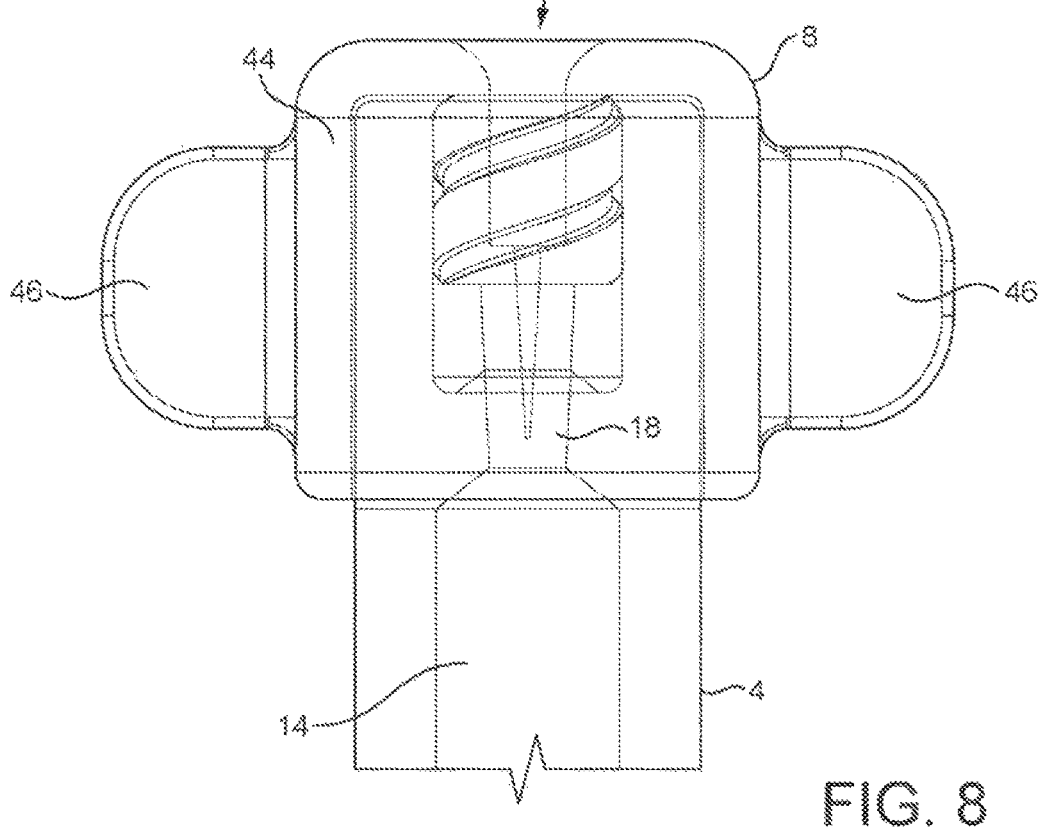
Figure 9:
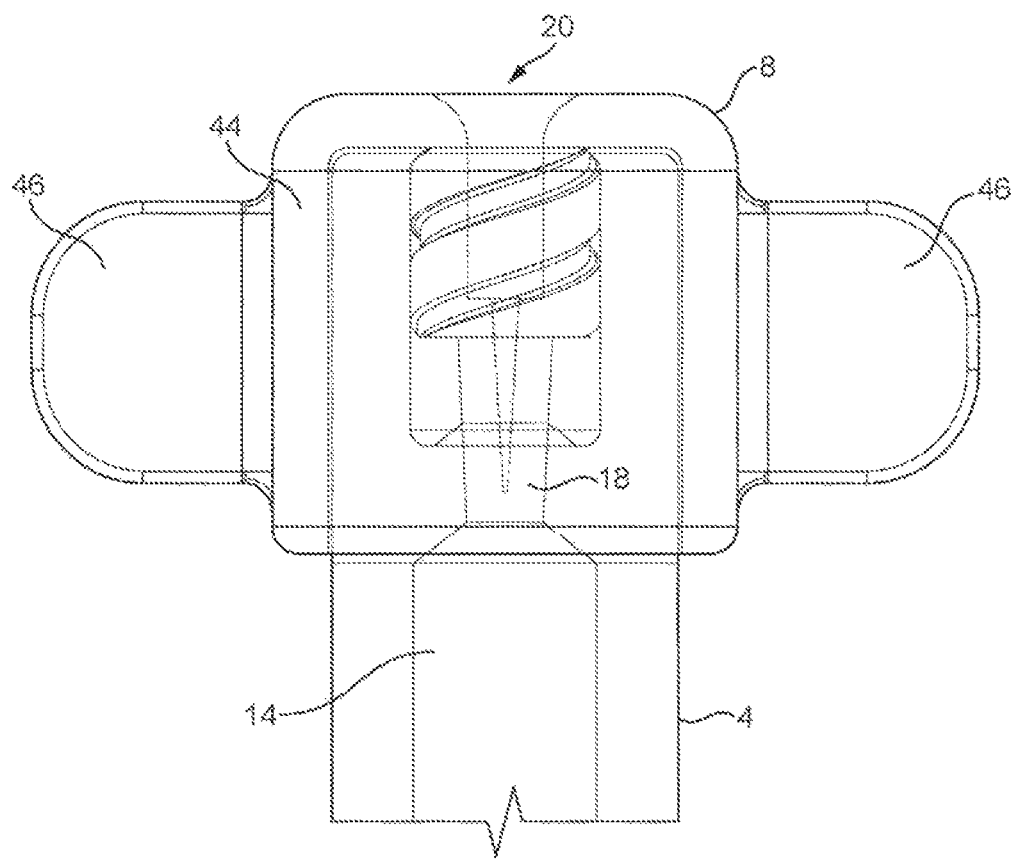

The inventors have designed several different embodiments of the end cap 8, as shown in FIGS. 7-9. As can be seen, the size (and surface area) of the side wings 46 increases from FIGS. 7 to 9.

Advantages of the syringe assembly 2 reside in the fact that it allows a medicament for buccal administration to be stored safely therein (i.e. pre-filled), without the risk of the medicament leaking or the solvent (e.g. ethanol) evaporating due to the threaded cap 8. Additionally, the medicament can be administered quickly to the patient without the user needing to pause to measure a dose. The positioning of the internal threaded section 38 ensures that the inside of a patient's mouth is not damaged. Additionally, the syringe 2 does not allow a user to attach the syringe 2 to a needle or drip and so removes any risk of a medicament intended for buccal administration being administered intravenously, which could be dangerous.

The invention claimed is:

1. A needleless syringe assembly comprising:
    a syringe barrel comprising an inner chamber filled or adapted to be filled with medicament, and a channel in fluid communication with the chamber and through which medicament is dispensed; and
    an end cap configured to be removably attached to the syringe barrel, characterised in that:
    the end cap comprises a body, two wings extending transversely therefrom and threads disposed directly between the two wings and the barrel comprises an internal threaded section which mutually engages with the threaded section on the end cap to thereby create a seal, which prevents the flow of medicament therethrough,
    the syringe assembly comprising a single unit dose syringe assembly pre-filled with medicament and configured to dispense substantially all of the medicament in a single delivery,
    the syringe assembly further comprises:
        a plunger configured to slide in the chamber and comprising a rod;
        a transversely extending projection disposed on the side of the plunger rod; and
        an indentation disposed along the inside of the chamber, or vice versa, wherein alignment of the projection and indentation correlates with a defined volume of medicament and thereby a dosage.

2. A syringe assembly according to claim 1, wherein the syringe barrel is incompatible with a Luer lock or a Luer slip.

3. A syringe assembly according to claim 1, wherein the syringe barrel does not comprise an external screw thread at least adjacent or towards the end of the barrel from which medicament is dispensed.

4. A syringe assembly according to claim 1, wherein the internal threaded section of the barrel is surrounded by a wall such that the threaded section is not radially exposed.

5. A syringe assembly according to claim 4, wherein the outside of the wall is smooth, and is an extension of the outer wall of the barrel.

6. A syringe assembly according to either claim 4, wherein the internal threaded section is disposed on the inside of the wall, and that the threaded section extends from the end of the barrel from which medicament is dispensed towards the channel, which leads to the chamber.

7. A syringe assembly according to claim 1, wherein the internal threaded section extends along the longitudinal axis of the barrel.

8. A syringe assembly according to claim 1, wherein the threaded section of the end cap comprises an external threaded section which screws into the internal threaded section of the barrel.

9. A syringe assembly according to claim 1, wherein the barrel comprises a transparent or translucent material.

10. A syringe assembly according to claim 1, wherein the plunger rod comprises first and second ends, wherein the first end is inserted into the chamber, and the second end comprises a thumb tab, and the barrel comprises a finger tab, which is configured to be engaged with the finger of one hand while also engaging the thumb tab with the thumb of the same hand.

11. The syringe assembly according to claim 1, for use in delivering a medicament, wherein the delivery is one of oral, buccal, sublingual, rectal, vaginal, topical, or transdermal.

* * * * *